United States Patent
Takamatsu et al.

(10) Patent No.: US 8,168,789 B2
(45) Date of Patent: May 1, 2012

(54) ORGANIC AMINE SALT OF 6-FLUORO-3-HYDROXY-2-PYRAZINE CARBONITRILE AND METHOD FOR PRODUCING THE SAME

(75) Inventors: Tamotsu Takamatsu, Toyama (JP); Kenji Yonezawa, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 148 days.

(21) Appl. No.: 12/679,496

(22) PCT Filed: Sep. 25, 2008

(86) PCT No.: PCT/JP2008/067251
§ 371 (c)(1),
(2), (4) Date: Mar. 25, 2010

(87) PCT Pub. No.: WO2009/041473
PCT Pub. Date: Apr. 2, 2009

(65) Prior Publication Data
US 2010/0286394 A1    Nov. 11, 2010

(30) Foreign Application Priority Data

Sep. 27, 2007  (JP) .................. 2007-251191

(51) Int. Cl.
*C07D 241/02*    (2006.01)

(52) U.S. Cl. ........................................ 544/409
(58) Field of Classification Search ............. 544/409
See application file for complete search history.

(56) References Cited

U.S. PATENT DOCUMENTS 6,800,629 B2    10/2004    Egawa et al.
2003/0130213 A1    7/2003    Egawa et al.

FOREIGN PATENT DOCUMENTS

| EP | 1 256 588 A1 | 11/2002 |
| EP | 1 805 131 B1 | 2/2011 |
| GB | 879259 | 10/1961 |
| JP | 2004 43371 | 2/2004 |
| WO | 01 60834 | 8/2001 |
| WO | WO 2005/097731 A2 | 10/2005 |

OTHER PUBLICATIONS

Examination Report issued Jul. 8, 2011, in New Zealand Patent Application No. 584157.

*Primary Examiner* — James O Wilson
*Assistant Examiner* — Douglas M Willis
(74) *Attorney, Agent, or Firm* — Oblon, Spivak, McClelland, Maier & Neustadt, L.L.P.

(57) ABSTRACT

Disclosed is an organic amine salt of 6-fluoro-3-hydroxy-2-pyrazinecarbonitrile, which is excellent in crystallinity and useful as a production intermediate for 6-fluoro-3-hydroxy-2-pyrazinecarboxamide.

8 Claims, No Drawings

ORGANIC AMINE SALT OF 6-FLUORO-3-HYDROXY-2-PYRAZINE CARBONITRILE AND METHOD FOR PRODUCING THE SAME

TECHNICAL FIELD

The present invention relates to an organic amine salt of 6-fluoro-3-hydroxy-2-pyrazinecarbonitrile, which is useful as an intermediate for the preparation of pharmaceuticals, and a process for producing such an amine salt.

BACKGROUND ART 6-fluoro-3-hydroxy-2-pyrazinecarboxamide (hereinafter referred to as T-705) is a compound which is useful for the prevention and treatment of viral infectious diseases, particularly influenza viral infectious diseases. It is known that T-705 can be produced from, for instance, 6-fluoro-3-hydroxy-2-pyrazinecarbonitrile (PATENT DOCUMENT 1).

As a process for producing 6-fluoro-3-hydroxy-2-pyrazinecarbonitrile, for instance, the following (1) and (2) processes are known: (1) a process in which 3,6-difluoro-2-pyrazinecarbonitrile is reacted with benzyl alcohol and the reaction product is debenzylated; and (2) a process in which 3,6-difluoro-2-pyrazinecarbonitrile is subjected to a reaction with water (PATENT DOCUMENT 1).

These known processes, however, have some disadvantages, for example, those as mentioned below: (A) the intermediate product 3-benzyloxy-6-fluoro-2-pyrazinecarbonitrile is a labile compound; (B) troublesome operations such as extraction, column chromatography and removal of the solvent by distillation are necessary; (C) harmful hydrogen fluoride is generated when the reaction mixture is acidified; and (D) the yield is low.

Further, it is not easy to isolate 6-fluoro-3-hydroxy-2-pyradinecarbonitrile from a reaction mixture in a high yield by a simple operation because this compound is soluble in water and many organic solvents.

PATENT DOCUMENT 1: International Publication No. WO 01/60834

DISCLOSURE OF THE INVENTION

Problems to be Solved by the Invention

A more excellent intermediate for the preparation of T-705 and a process for producing such an intermediate have been strongly desired.

Means for Solving the Problems

Under these circumstances, the present inventors have pursued concentrated studies on the subject matter and, as a result, found that an organic amine salt of 6-fluoro-3-hydroxy-2-pyrazinecarbonitrile has excellent crystallinity and can serve as a useful intermediate for the preparation of T-705. They have also found that an organic amine salt of 6-fluoro-3-hydroxy-2-pyrazinecarbonitrile can be produced easily in a high yield by reacting 3,6-difluoro-2-pyrazinecarbonitrile with water in the presence of a base and then adding an organic amine. These findings have led them to complete the present invention.

Advantages of the Invention

The organic amine salts of 6-fluoro-3-hydroxy-2-pyrazinecarbonitrile according to the present invention have excellent crystallinity, can be isolated from a reaction mixture in a high yield by a simple operation, and are useful as an intermediate for the preparation of T-705. Also, the process of producing the organic amine salts of 6-fluoro-3-hydroxy-2-pyrazinecarbonitrile according to the present invention has the advantages in that: (1) the process has no involvement of a labile intermediate; (2) no troublesome operations such as extraction, column chromatography and removal of the solvent by distillation are needed; (3) no harmful hydrogen fluoride is formed; (4) the yield is high; and (5) the obtained organic amine salts are high in purity. This process of the present invention, therefore, is useful as a process for industrially producing the organic amine salts of 6-fluoro-3-hydroxy-2-pyrazinecarbonitrile.

BEST MODE FOR CARRYING OUT THE INVENTION

The present invention will be explained in detail below.

In the present description of the invention, the "organic amines" designate the following unless otherwise noted: tertiary amines such as trimethylamine, triethylamine, tripropylamine, tributylamine, tribenzylamine and N,N-dimethylcyclohexylamine; secondary amines such as dimethylamine, diethylamine, dipropylamine, dibutylamine, dibenzylamine, N-benzylmethylamine and dicyclohexylamine; primary amines such as methylamine, ethylamine, propylamine, butylamine, benzylamine and aniline; and pyridine and the like.

In the organic amine salts of 6-fluoro-3-hydroxy-2-pyrazinecarbonitrile provided as the compounds of the present invention, the following compounds are preferred.

The compounds having as an organic amine a secondary amine, particularly dipropylamine, dibutylamine, dicyclohexylamine, dibenzylamine and N-benzylmethylamine are preferred, and those having dicyclohexylamine are especially preferred.

A preferred production process according to the present invention is shown below.

A process for producing an organic amine salt of 6-fluoro-3-hydroxy-2-pyrazinecarbonitrile by reacting 3,6-difluoro-2-pyrazinecarbonitrile with water in the present of a base and then adding an organic amine, wherein a secondary amine is used as the organic amine, is preferred. More preferred is a process using dipropylamine, dibutylamine, dicyclohexylamine, dibenzylamine or N-benzylmethylamine as a secondary amine. A process using dicyclohexylamine is even more preferred.

Next, a production process according to the present invention is explained.

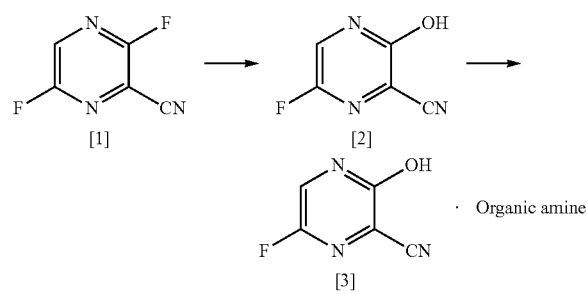

An organic amine salt of the compound of the formula [3] can be produced by reacting the compound of the formula [1]

with water in the presence of a base to form the compound of the formula [2], and then further reacting it with an organic amine.

This process of the present invention will be described in detail below.

[Step 1]

The compound of the formula [2] can be produced by reacting the compound of the formula [1] with water in the presence of a base.

This reaction is usually carried out in the presence of a solvent. All types of solvents can be used as far as they do not exert any adverse effect to the reaction. Examples of such solvents include nitriles such as acetonitrile; aromatic hydrocarbons such as benzene, toluene and xylene; ethers such as dioxane, tetrahydrofuran, ethylene glycol dimethyl ether and diethylene glycol dimethyl ether; ketones such as acetone and 2-butanone; alcohols such as ethanol, propanol, 2-propanol and butanol; amides such as N,N-dimethylformamide and N,N-dimethylacetamide; and sulfoxides such as dimethyl sulfoxide. Mixtures of these solvents can be used. The preferred solvents for use in the present invention are aromatic hydrocarbons, ethers, amides and sulfoxides. Among these solvents, amides and sulfoxides are more preferred, and N,N-dimethylformamide is even more preferred. The amount of the solvent used is not definitely specified, but it is used desirably in an amount 1 to 50 times (v/w), preferably 1 to 15 times (v/w) per the amount of the compound of the formula [1].

The bases used in the above reaction are not subject to any specific restrictions provided that they are the reagents commonly used for hydroxylation in the nucleophilic displacement reactions of the aromatic halogen compounds. Examples of such bases include organic bases such as diisopropylethylamine and triethylamine; quaternary ammonium hydroxides such as benzyltrimethylammonium hydroxide; carboxylates such as potassium formate, sodium formate, formic acid-triethylamine, potassium acetate, sodium acetate, acetic acid-triethylamine, sodium propionate, sodium hexanoate, sodium benzoate and benzoic acid-triethylamine; and inorganic bases such as sodium hydroxide, potassium hydroxide, sodium carbonate, potassium carbonate, sodium bicarbonate, potassium bicarbonate, dipotassium hydrogenphosphate and tripotassium phosphate. Carboxylates are preferred for use as a base. Potassium formate, formic acid-triethylamine, potassium acetate and acetic acid-triethylamine are more preferred. In the present invention, a base is used in an amount of 1 mole or more, desirably 1 to 10 moles to one mole of the compound of the formula [1].

Carboxylates may be prepared in the reaction system.

The amount of water used for the above reaction is not specifically defined; it suffices to use water in an amount of one mole or more, desirably 1 to 50 moles to one mole of the compound of the formula [1].

In case of using a carboxylate, it is possible to produce the compound of the formula [2] by reacting the compound of the formula [1] with the carboxylate in the absence of water and then conducting reaction with water.

The reaction temperature is not specifically defined, but it is required to be not higher than 200° C., desirably between 0 and 150° C.

The reaction time is also not specified in the present invention; a duration between 5 minutes and 50 hours is enough for the reaction. The preferred reaction time is 5 minutes to 24 hours.

The compound of the formula [2] can be isolated and purified, but it is desirably offered to use for the next reaction without isolation.

[Step 2]

An organic amine salt of the compound of the formula [3] can be produced by subjecting the compound of the formula [2] to a reaction with an organic amine.

This reaction is usually carried out in the presence of a solvent. All types of solvent can be used for the reaction provided that their presence is not detrimental to the reaction in any way. Examples of such solvents are nitriles such as acetonitrile; aromatic hydrocarbons such as benzene, toluene and xylene; ethers such as dioxane, tetrahydrofuran, ethylene glycol dimethyl ether and diethylene glycol dimethyl ether; ketones such as acetone and 2-butanone; alcohols such as methanol, ethanol, propanol, 2-propanol and butanol; amides such as N,N-dimethylformamide and N,N-dimethylacetamide; sulfoxides such as dimethyl sulfoxide; and water. Mixtures of these solvents are also usable. A preferred solvent for use in the present invention is a mixture of at least one solvent selected from aromatic hydrocarbons, ketones, alcohols, amides and sulfoxides with water. A mixture of an aromatic hydrocarbon, a ketone or an amide with water is more preferred, and a mixture of toluene, acetone or N,N-dimethylformamide with water is even more preferred. The amount of the solvent used in the present invention is not defined, but it is desirably 1 to 100 times (v/w), preferably 1 to 50 times (v/w) per the amount of the compound of the formula [2].

The amount of an organic amine used in the above reaction is also not defined, but use of an organic amine in an amount of one mole or more to one mole of the compound of the formula [2] is enough. Desirably an organic amine is used in an amount of one to 2 moles to one mole of the compound of the formula [2].

The reaction temperature is not specifically defined, but it is required to be not higher than 150° C., desirably between 0 and 100° C.

The reaction time is also not specified in the present invention; a duration between one minute and 50 hours is enough for the reaction. The preferred reaction time is one minute to 24 hours.

This reaction is desirably carried out under a basic condition. For instance, desirably a base selected from ammonia water, potassium hydroxide, sodium hydroxide, potassium acetate and sodium acetate is added to the reaction system.

The organic amine salts of the compounds of the formula [3] obtained from the above-described production process can be isolated by filtering off and collecting the solids.

The compound of the formula [1] used as a starting material of the product of the present invention can be produced from 3,6-dichloro-2-pyrazinecarbonitrile or the like by, for instance, the process disclosed in PATENT DOCUMENT 1. 3,6-dichloro-2-pyrazinecarbonitrile can be produced by combining the per se known processes (PATENT DOCUMENT 1). For instance, the above compound can be produced by reacting 3-hydroxy-6-nitro-2-pyrazinecarboxamide or 6-bromo-3-hydroxy-2-pyrazinecarboxamide with a halogenating agent such as phosphorus oxychloride. In these productions, the compound of the formula [1] and 3,6-dichloro-2-pyrazinecarbonitrile can be isolated and purified, but they may be directly used for the next reaction without isolation.

In the process for producing the compound of the formula [3] from the compound of the formula [1], the yield of the production process described in PATENT DOCUMENT 1 was 46% (PATENT DOCUMENT 1; Example II-5(a)).

In contrast, in the process for producing an organic amine salt of the compound of the formula [3] from the compound of the formula [1], the yield of the production process of the present invention was as high as 83% (Example 1-1).

Thus the production process of the present invention is high in yield and useful as an industrial production process.

The compounds of the formula [2] and their salts and the compounds of the formula [3] include the tautomer of 6-fluoro-3-oxo-3,4-dihydro-2-pyrazinecarbonitrile. The present invention embraces such a tautomer, and it is possible in this invention to use hydrates, solvates and all the crystal forms.

EXAMPLES

The present invention will be further explained by showing the Examples as well as the Preparation Examples, but these examples are merely intended to be illustrative and not to be construed as limiting the scope of the present invention in any way. DMSO-$d_6$: dimethyl sulfoxide-$d_6$

Example 1-1

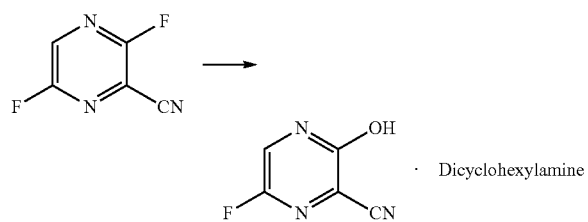

To a 17.5 ml N,N-dimethylformamide solution of 5.0 g of 3,6-difluoro-2-pyrazinecarbonitrile, a 3.8 ml water solution of 7.83 g of potassium acetate was added dropwise at 25 to 35° C., and the solution was stirred at the same temperature for 2 hours. 0.38 ml of ammonia water was added to the reaction mixture, and then 15 ml of water and 0.38 g of active carbon were added. The insolubles were filtered off and the filter cake was washed with 11 ml of water. The filtrate and the washing were joined, the pH of this solution was adjusted to 9.4 with ammonia water, and 15 ml of acetone and 7.5 ml of toluene were added. Then 7.71 g of dicyclohexylamine was added dropwise and the solution was stirred at 20 to 30° C. for 45 minutes. Then 15 ml of water was added dropwise, the solution was cooled to 10° C., and the precipitate was filtered and collected to give 9.44 g of dicyclohexylamine salt of 6-fluoro-3-hydroxy-2-pyradinecarbonitrile as a lightly yellowish white solid product.

$^1$H-NMR (DMSO-$d_6$) δ values: 1.00-1.36 (10H, m), 1.56-1.67 (2H, m), 1.67-1.81 (4H, m), 1.91-2.07 (4H, m), 3.01-3.18 (2H, m), 8.03-8.06 (1H, m), 8.18-8.89 (1H, broad)

Example 1-2

4.11 ml of acetic acid was added at 5 to 15° C. to a 17.5 ml N,N-dimethylformamide solution of 5.0 g of 3,6-difluoro-2-pyrazinecarbonitrile. Then 7.27 g of triethylamine was added dropwise and the solution was stirred for 2 hours. 3.8 ml of water and 0.38 ml of ammonia water were added to the reaction mixture, and then 15 ml of water and 0.38 g of active carbon were added. The insolubles were filtered off and the filter cake was washed with 11 ml of water. The filtrate and the washing were joined, the pH of the joined solution was adjusted to 9.2 with ammonia water, and 15 ml of acetone and 7.5 ml of toluene were added to the solution, followed by dropwise addition of 7.71 g of dicyclohexylamine. Then 15 ml of water was added dropwise, the solution was cooled to 5° C., and the precipitate was filtered and collected to give 9.68 g of dicyclohexylamine salt of 6-fluoro-3-hydroxy-2-pyrazinecarbonitrile as a slightly yellowish white solid product.

Examples 2 to 5

The compounds shown in Table 1 were obtained in the same way as in Example 1-1.

TABLE 1

![structure]

· Organic amine

| Example No. | Organic amine | Example No. | Organic amine |
|---|---|---|---|
| 2 | Dipropylamine | 4 | Dibenzylamine |
| 3 | Dibutylamine | 5 | N-benzylmethylamine |

Dipropylamine salt of 6-fluoro-3-hydroxy-2-pyrazinecarbonitrile $^1$H-NMR (DMSO-$d_6$) δ values: 0.39 (6H, t, J=7.5 Hz), 1.10 (4H, sex, J=7.5 Hz), 2.30-2.38 (4H, m), 7.54 (1H, d, J=8.3 Hz)

Dibutylamine salt of 6-fluoro-3-hydroxy-2-pyrazinecarbonitrile $^1$H-NMR (DMSO-$d_6$) δ values: 0.36 (6H, t, J=7.3 Hz), 0.81 (4H, sex, J=7.3 Hz), 0.99-1.10 (4H, m), 2.32-2.41 (4H, m), 7.53 (1H, d, J=8.3 Hz)

Dibenzylamine salt of 6-fluoro-3-hydroxy-2-pyrazinecarbonitrile $^1$H-NMR (DMSO-$d_6$) δ values: 4.17 (4H, s), 7.34-7.56 (10H, m), 8.07 (1H, d, J=8.3 Hz)

N-benzylmethylamine salt of 6-fluoro-3-hydroxy-2-pyrazinecarbonitrile $^1$H-NMR (DMSO-$d_6$) δ values: 2.57 (3H, s), 4.14 (2H, s), 7.37-7.53 (5H, m), 8.02-8.08 (1H, m)

Preparation Example 1

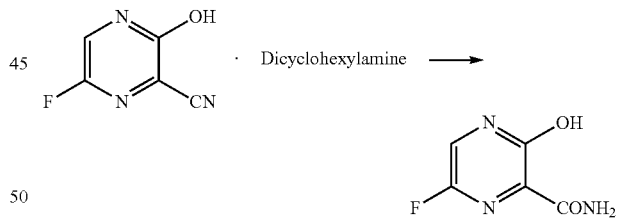

300 ml of toluene was added to a 600 ml water solution of 37.5 g of sodium hydroxide. Then 150 g of dicyclohexylamine salt of 6-fluoro-3-hydroxy-2-pyrazinecarbonitrile was added at 15 to 25° C. and the solution was stirred at the same temperature for 30 minutes. The water layer was separated and washed with toluene, and then 150 ml of water was added, followed by dropwise addition of 106 g of a 30% hydrogen peroxide solution at 15 to 30° C. and one-hour stirring at 20 to 30° C. Then 39 ml of hydrochloric acid was added, the seed crystals were added at 40 to 50° C., and 39 ml of hydrochloric acid was further added dropwise at the same temperature. The solution was cooled to 10° C. the precipitate was filtered and collected to give 65.6 g of 6-fluoro-3-hydroxy-2-pyrazinecarboxamide as a slightly yellowish white solid.

$^1$H-NMR (DMSO-d$_6$) δ values: 8.50 (1H, s), 8.51 (1H, d, J=7.8 Hz), 8.75 (1H, s), 13.41 (1H, s)

INDUSTRIAL APPLICABILITY

The organic amine salts of 6-fluoro-3-hydroxy-2-pyrazinecarbonitrile of the present invention are excellent in crystallinity and are useful as an intermediate for the production of 6-fluoro-3-hydroxy-2-pyrazinecarboxamide.

The invention claimed is:

1. An organic amine salt of 6-fluoro-3-hydroxy-2-pyrazinecarbonitrile.

2. The organic amine salt according to claim 1, wherein the organic amine is a secondary amine.

3. The organic amine salt according to claim 2, wherein the secondary amine is dipropylamine, dibutylamine, dicyclohexylamine, dibenzylamine or N-benzylmethylamine.

4. The organic amine salt according to claim 2, wherein the secondary amine is dicyclohexylamine.

5. A process for producing an organic amine salt of 6-fluoro-3-hydroxy-2-pyrazinecarbonitrile, which comprises reacting 3,6-difluoro-2-pyrazinecarbonitrile with water in the presence of a base, and then forming a salt with an organic amine.

6. The process according to claim 5, wherein the organic amine is a secondary amine.

7. The process according to claim 6, wherein the secondary amine is dipropylamine, dibutylamine, dicyclohexylamine, dibenzylamine or N-benzylmethylamine.

8. The process according to claim 6, wherein the secondary amine is dicyclohexylamine.

* * * * *